（12) United States Patent
Troxler et al.

(10) Patent No.: US 11,707,228 B2
(45) Date of Patent: Jul. 25, 2023

(54) SYSTEMS AND METHODS FOR INTRA-PROCEDURAL CARDIAC PRESSURE MONITORING

(71) Applicant: EVALVE, INC., Santa Clara, CA (US)

(72) Inventors: Lauren Troxler, San Francisco, CA (US); Chad Abunassar, San Francisco, CA (US); Jhey Samson, Milpitas, CA (US); Eymard Burlaza, Lathrop, CA (US); Manish Gada, Santa Clara, CA (US)

(73) Assignee: EVALVE, INC., Santa Clara, CA (US)

( * ) Notice: Subject to any disclaimer, the term of this patent is extended or adjusted under 35 U.S.C. 154(b) by 280 days.

(21) Appl. No.: 17/033,235

(22) Filed: Sep. 25, 2020

(65) Prior Publication Data

US 2021/0093256 A1    Apr. 1, 2021

Related U.S. Application Data

(60) Provisional application No. 62/906,581, filed on Sep. 26, 2019.

(51) Int. Cl.
*A61B 5/0215* (2006.01)
*A61B 5/00* (2006.01)
(Continued)

(52) U.S. Cl.
CPC .......... *A61B 5/6852* (2013.01); *A61B 5/0215* (2013.01); *A61B 5/6869* (2013.01);
(Continued)

(58) Field of Classification Search
CPC ........................................ A61B 5/0215–02158
See application file for complete search history.

(56) References Cited

U.S. PATENT DOCUMENTS 3,378,010 A    4/1968 Codling et al.
3,874,388 A    4/1975 King et al.
(Continued)

FOREIGN PATENT DOCUMENTS

CA    2 296 317 C    1/2009
EP    0 558 031 B1    9/1993
(Continued)

OTHER PUBLICATIONS

U.S. Appl. No. 16/321,221 (US 2019/0167197), filed Jan. 28, 2019 (Jun. 6, 2019).
(Continued)

*Primary Examiner* — Meredith Weare
(74) *Attorney, Agent, or Firm* — Sleman & Lund LLP

(57) ABSTRACT

Delivery system for fixation device, including guide catheter with proximal end portion having proximal end port, distal end portion having distal end port, and inner surface defining inner lumen extending in fluid communication between proximal end port and distal end port. Delivery catheter extending through the inner lumen to define annular space between outer surface of the delivery catheter and inner surface of the guide catheter. A pressure sensor proximate the proximal end portion in fluid communication with the annual space to monitor fluid pressure. The distal end portion of the guide catheter includes flow passages in fluid communication between an exterior of the distal end portion and the annular space.

20 Claims, 12 Drawing Sheets

(51) Int. Cl.
*A61M 25/00* (2006.01)
*A61M 25/06* (2006.01)

(52) U.S. Cl.
CPC ....... *A61B 5/6884* (2013.01); *A61B 2560/066* (2013.01); *A61M 25/005* (2013.01); *A61M 25/0026* (2013.01); *A61M 2025/0002* (2013.01); *A61M 2025/0003* (2013.01); *A61M 2025/0681* (2013.01)

(56) References Cited

U.S. PATENT DOCUMENTS

| | | |
|---|---|---|
| 4,007,743 A | 2/1977 | Blake |
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |
| 5,069,679 A | 12/1991 | Taheri |
| 5,098,440 A | 3/1992 | Stead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,674 B1 | 7/2002 | Bowser et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,556,632 B2 | 7/2009 | Zadno |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,972,323 B1 | 7/2011 | Bencini et al. |
| 7,981,139 B2 | 7/2011 | Martin et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,510,829 B2 | 12/2016 | Goldfarb et al. |
| 10,076,415 B1 | 9/2018 | Metchik et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |

(56) References Cited

U.S. PATENT DOCUMENTS

| | | |
|---|---|---|
| 2004/0092962 A1 | 5/2004 | Thornton et al. |
| 2004/0243057 A1* | 12/2004 | Vinten-Johansen ...... A61M 25/10 604/97.01 |
| 2005/0267493 A1 | 12/2005 | Schreck et al. |
| 2007/0038293 A1 | 2/2007 | St. Goar et al. |
| 2011/0301699 A1 | 12/2011 | Saadat |
| 2013/0030303 A1 | 1/2013 | Ahmed et al. |
| 2013/0197621 A1 | 8/2013 | Ryan et al. |
| 2013/0281979 A1 | 10/2013 | Amim |
| 2015/0133800 A1 | 5/2015 | McCaffrey et al. |
| 2015/0196210 A1 | 7/2015 | McCaffrey et al. |
| 2016/0367787 A1* | 12/2016 | Van Hoven ............. A61F 2/246 |
| 2017/0042546 A1 | 2/2017 | Goldfarb et al. |
| 2017/0049455 A1 | 2/2017 | Seguin |
| 2017/0080178 A1* | 3/2017 | O'Connell ........... A61M 25/005 |
| 2017/0100250 A1 | 4/2017 | Marsot et al. |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |
| 2018/0146964 A1 | 5/2018 | Garcia et al. |
| 2018/0193042 A1* | 7/2018 | Wilson ..................... A61B 17/22 |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0256848 A1 | 9/2018 | Ramanathan |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0046761 A1* | 2/2019 | Rogers ............... A61B 5/02158 |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernandez et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | | |
|---|---|---|---|
| EP | 1 208 867 A2 | 5/2002 | |
| EP | 1 383 448 B1 | 6/2008 | |
| FR | 2 768 324 A1 | 3/1999 | |
| FR | 2 768 325 B1 | 11/1999 | |
| WO | WO 91/01689 A1 | 2/1991 | |
| WO | WO 92/12690 A1 | 8/1992 | |
| WO | WO 94/018893 A1 | 9/1994 | |
| WO | WO 96/32882 A1 | 10/1996 | |
| WO | WO 97/27807 A1 | 8/1997 | |
| WO | WO 98/07375 A1 | 2/1998 | |
| WO | WO 99/07354 A2 | 2/1999 | |
| WO | WO 99/13777 A1 | 3/1999 | |
| WO | WO 99/15223 A1 | 4/1999 | |
| WO | WO 00/03759 A2 | 1/2000 | |
| WO | WO 00/60995 A2 | 10/2000 | |
| WO | WO 01/28432 A1 | 4/2001 | |
| WO | WO 03/020179 A1 | 3/2003 | |
| WO | WO 03/049619 A2 | 6/2003 | |
| WO | WO 2015/057289 A1 | 4/2015 | |
| WO | WO 2016/178722 A1 | 11/2016 | |
| WO | WO-2018022919 A1 * | 2/2018 | ......... A61B 17/0057 |
| WO | WO 2018/093663 A1 | 5/2018 | |

OTHER PUBLICATIONS

U.S. Appl. No. 16/321,221, dated Nov. 19, 2020 Final Office Action.

U.S. Appl. No. 16/321,221, dated Sep. 11, 2020 Response to Non-Final Office Action.

U.S. Appl. No. 16/321,221, dated Jun. 11, 2020 Non-Final Office Action.

International Search Report dated Dec. 8, 2020 in International Application No. PCT/US2020/052646.

International Search Report dated Jan. 2, 2018 in International Application No. PCT/US2017/044224.

* cited by examiner

| SGC Test Groups | N | Soft Tip ID | Channel to Channel | Channel Width | Channel Orientation |
|---|---|---|---|---|---|
| Lo | 5 | 0.205" | 0.226" | .057" | 45° from SGC +/- Curve Plane |
| Nominal | 5 | 0.206" | 0.229" | .060" | 45° from SGC +/- Curve Plane |

FIG. 9

| Nominal (All conditions) | Mean (mmHg) | Stdev (mmHg) | Prob<W Test for Normality | 95/95 Upper TI (mmHg) |
|---|---|---|---|---|
| Max | 1.02 | 0.82 | 0.051 | 3.13 |
| Mean | 0.75 | 0.47 | 0.452 | 1.94 |
| Min | 1.45 | 1.10 | 0.246 | 4.34 |

FIG. 11A

| Lo (All conditions) | Mean (mmHg) | Stdev (mmHg) | Prob<W Test for Normality | 95/95 Upper TI (mmHg) |
|---|---|---|---|---|
| Max | 1.29 | 1.21 | 0.026 | 4.38 |
| Mean | 0.39 | 0.33 | 0.161 | 1.24 |
| Min | 0.62 | 0.36 | 0.025 | 1.54 |

FIG. 11B

SYSTEMS AND METHODS FOR INTRA-PROCEDURAL CARDIAC PRESSURE MONITORING

CROSS-REFERENCE TO RELATED APPLICATIONS

This application claims the benefit of U.S. Provisional Application No. 62/906,581, filed Sep. 26, 2019, the content of which is hereby incorporated by reference in its entirety.

BACKGROUND

During cardiac procedures, blood pressure is often measured and monitored at different areas of the heart to aid in initial diagnosis, to confirm procedural safety, and to verify procedural efficacy. For example, in the context of a mitral valve repair or replacement procedure, right-atrial pressure, left-atrial pressure, and pressure gradients across the mitral valve can be measured during and after the procedure.

Typically, such pressure monitoring is achieved through the use of a pressure wire or fractional flow reserve ("FFR") wire that is inserted into the targeted treatment area of the heart. For example, an operator can introduce a pressure wire into a pulmonary vein to monitor left atrial pressure during a mitral valve repair or replacement procedure. In some circumstances, indirect imaging-based methods are also used to calculate pressure.

Although some degree of intra-procedural pressure monitoring is enabled through these methods, there remains a need for continued improvement. For example, the use of a pressure wire or FFR wire in conjunction with guidewires, catheters, and other components of the procedure can be cumbersome and can increase procedure time. Additionally, in procedures that involve crossing of the septum, monitoring pressure at the targeted area using conventional techniques can require a larger septal puncture, or a second puncture to provide access for a pressure wire to the targeted area.

Accordingly, in many circumstances, the potential benefits of monitoring cardiac pressure intra-procedurally are negated and offset by the foregoing problems.

International Application WO2018/022919, the disclosure of which is hereby incorporated by reference in its entirety, describes intra-procedural cardiac pressure monitoring systems for delivering a pressure monitoring sensor to the heart using routing lumens or grooves in a delivery catheter. Such systems can eliminate the need for a second septal puncture to deliver the pressure sensor to the heart. However, there remains a continued need for alternative pressure measurement systems.

The subject matter disclosed herein is not limited to embodiments that solve any issues or that operate only in environments such as those described above. Rather, this background is only provided to illustrate one exemplary technology area where embodiments described herein can be practiced.

SUMMARY

The purpose and advantages of the disclosed subject matter will be set forth in and apparent from the description that follows, as well as will be learned by practice of the disclosed subject matter. For purpose of illustration and not limitation, the various embodiments described herein relate to interventional delivery systems configured for delivering an interventional device (such as, a valve repair or replacement device, annuloplasty ring, chord replacement or repair device, spacer device, occlusion device, suturing device, or other cardiac interventional device) to a targeted treatment area. The delivery systems are configured to enable the monitoring of hemodynamic properties before, during, and/or after deployment of the interventional device. Additional advantages of the disclosed subject matter will be realized and attained by the methods and systems particularly pointed out in the written description and claims hereof, as well as from the appended drawings.

To achieve these and other advantages, and in accordance with the purpose of the disclosed subject matter, as embodied and broadly described, the disclosed subject matter includes a delivery system for a fixation device, the delivery system including a guide catheter with a proximal end portion having a proximal end port, a distal end portion having a distal end port, and an inner surface defining an inner lumen extending in fluid communication between the proximal end port and the distal end port. The system further includes a delivery catheter extending through the inner lumen of the guide catheter to define an annular space between an outer surface of the delivery catheter and the inner surface of the guide catheter. The system further includes a pressure sensor proximate the proximal end portion of the guide catheter in fluid communication with the annual space to monitor fluid pressure within the annular space. The distal end portion of the guide catheter includes a plurality flow passages in fluid communication between an exterior of the distal end portion of the guide catheter and the annular space.

In accordance with an aspect of the disclosed subject matter, the plurality of flow passages collectively can have a total flow area between the exterior of the distal end portion and the annular space of between about 0.0021 in$^2$ and 0.0031 in$^2$. Additionally, the delivery system can include a fixation device removably coupled to a distal end of the delivery catheter and configured for fixation to leaflets of a native valve.

As embodied herein, the plurality of flow passages can include a number of flow channels spaced about a perimeter of the distal end port. The number of flow channels can be spaced equally about the perimeter of the distal end port. For example, the number of flow channels can be four flow channels. For purpose of example and not limitation, each flow channel can have a width of about 0.056 to 0.062 inches. As embodied herein, each flow channel can have a width of about 0.059 inches. Furthermore, each flow channel can have a depth from the perimeter of the distal end port. For purpose of example and not limitation, the depth can be between about 0.009 to about 0.0125 inches. As embodied herein, each flow channel can have a depth of about 0.011 inches.

The distal end port can have an inner diameter substantially equal to an outer diameter along a distal end portion of the delivery catheter. For purpose of example and not limitation, the inner diameter can be between about 0.204 and about 0.209 inches. As embodied herein, the inner diameter can be about 0.206 inches. The distal end portion of the guide catheter can include a distal tip member having the distal end port and the flow channels defined therein. The distal tip member can have a durometer hardness measurement of 40 D up to 55 D or greater. Additionally, or alternatively, the distal tip member can be made of polyether block amide (e.g. Pebax) or the like.

In accordance with another aspect, the guide catheter can be a steerable guide catheter. The steerable guide catheter can include a steering mechanism with a plurality of cables extending a length of the guide catheter. The steering mechanism can be adapted to bend the distal end portion of the guide catheter in at least one reference plane. Each flow channel can be offset circumferentially about the perimeter of the distal end port from the reference plane. For purpose of example, and as embodied herein, each flow channel can be offset circumferentially by about 45° from the reference plane.

As embodied herein, the proximal end portion of the guide catheter can include a luer connector in fluid communication with the annular space. The pressure sensor can be removably connectable to the luer connector. The pressure sensor can be a pressure transducer. Furthermore, the proximal end portion can include a hemostasis valve to seal a proximal end of the annual space.

Additionally, or alternatively, and in accordance with another aspect of the disclosed subject matter, the plurality of flow passages can include a number of flow openings defined through a wall of the guide catheter in fluid communication between the exterior of the distal end portion and the annular space. Furthermore, the distal end portion of the guide catheter can include a braided reinforcement.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the containers and methods of the disclosed subject matter. Together with the description, the drawings serve to explain the principles of the disclosed subject matter.

BRIEF DESCRIPTION OF THE DRAWINGS

FIG. 9 is a chart depicting measured characteristics of exemplary guide catheters tested with delivery systems in accordance with the disclosed subject matter.

FIGS. 11A and 11B are charts depicting statistical analysis data obtained during testing of exemplary delivery systems in accordance with the disclosed subject matter.

DETAILED DESCRIPTION

Figure 1:
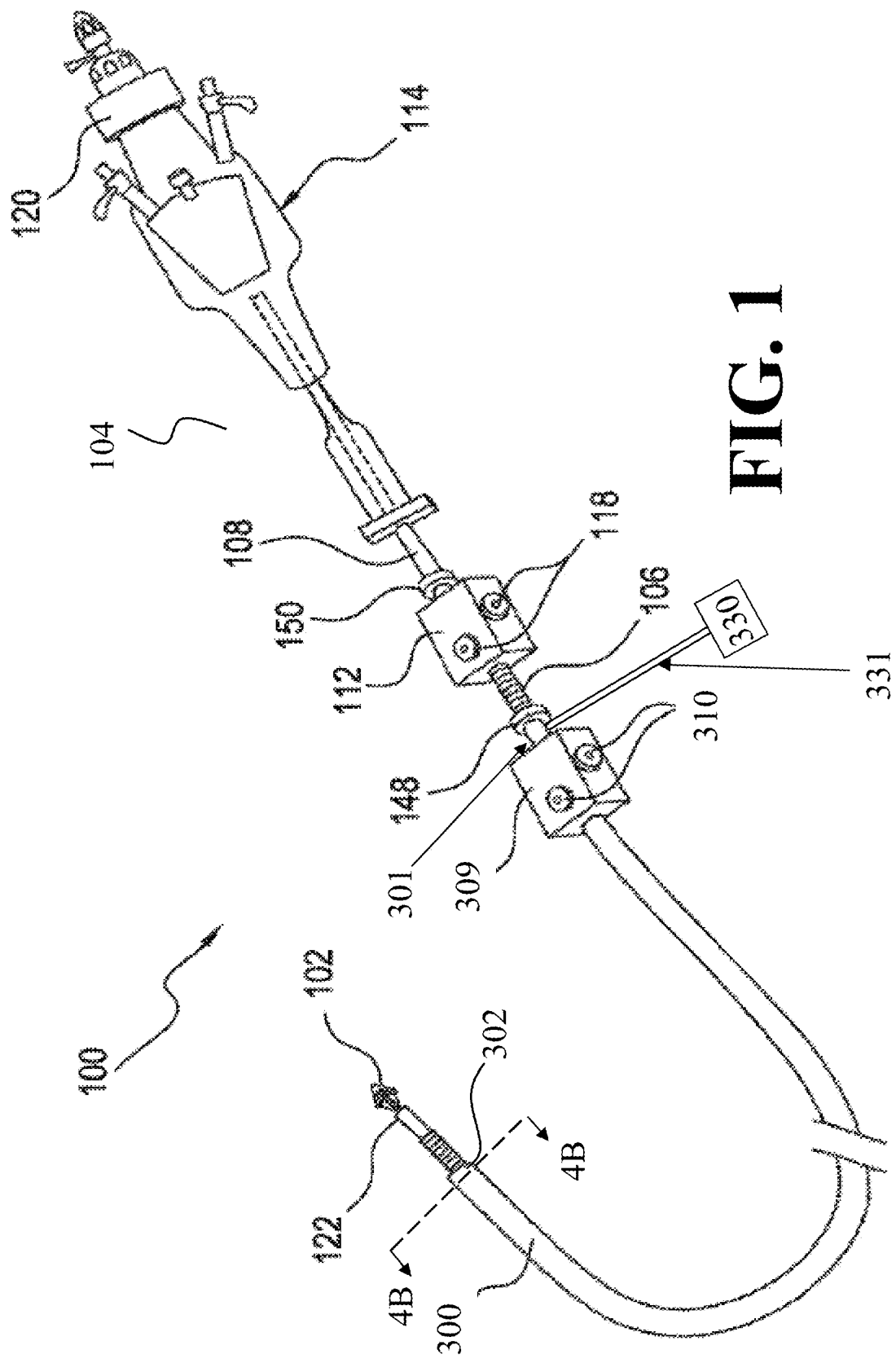
FIG. 1 is a perspective view of an exemplary delivery system in accordance with the disclosed subject matter.

Reference will now be made in detail to the various exemplary embodiments of the disclosed subject matter, which are illustrated in the accompanying drawings. The structure and corresponding method of operation of the disclosed subject matter will be described in conjunction with the detailed description of the system.

The disclosed subject matter is directed to devices, systems, and methods enabling intra-procedural monitoring of cardiac pressure and related hemodynamics. As embodied herein, pressure monitoring can be enabled before, during, and/or after a cardiac procedure. Although the embodiments described herein are directed to a mitral valve repair procedure for purpose of illustration and not limitation, it will be understood that the related principles and/or components can also be applied within the context of another cardiac procedure, such as a mitral valve replacement, tricuspid valve repair or replacement, chordae tendineae repair or replacement, septal defect repair, occlusion, leaflet modification, leaflet plication, or other cardiac procedure where the monitoring of blood pressure or other hemodynamic properties is desired.

In addition, although reference is made to "intra-procedural" pressure monitoring, pre and/or post-procedural pressure monitoring also is contemplated.

Further, although reference is made to various components for measuring blood pressure, it will be understood that such pressure monitoring can, alternatively or additionally, include blood flow monitoring and/or the monitoring of other hemodynamic properties. Accordingly, the terms "sensor," "sensor wire," "transducer," and the like, as user herein, typically refer to pressure-sensing devices, but in other embodiments, can additionally or alternatively refer to flow sensing devices and/or devices configured for measuring other hemodynamic properties. In addition, although various descriptions make reference to "sensor" in the singular, it will be understood that alternative embodiments include one or more sensor arrays having multiple different sensors arranged together as a sensor array unit.

Delivery systems in accordance with the disclosed subject matter generally include a guide catheter with a proximal end portion having a proximal end port, a distal end portion having a distal end port, and an inner surface defining an inner lumen extending in fluid communication between the proximal end port and the distal end port. The system further includes a delivery catheter extending through the inner lumen of the guide catheter to define an annular space between an outer surface of the delivery catheter and the inner surface of the guide catheter. The system further includes a pressure sensor proximate the proximal end portion of the guide catheter in fluid communication with the annual space to monitor fluid pressure within the annular space. The distal end portion of the guide catheter includes a plurality flow passages in fluid communication between an exterior of the distal end portion of the guide catheter and the annular space. In accordance with an aspect of the disclosed subject matter, the plurality of flow passages can collectively have a total flow area between the exterior of the distal end portion and the annular space of between about 0.0021 in$^2$ and 0.0031 in$^2$. In accordance with another aspect of the disclosed subject matter, a fixation device can be removably coupled to a distal end of the delivery catheter and configured for fixation to leaflets of a native valve can be provided.

The accompanying figures, where like reference numerals refer to identical or functionally similar elements throughout the separate views, serve to further illustrate various embodiments and to explain various principles and advantages all in accordance with the disclosed subject matter.

For purpose of illustration, and not limitation, reference is made to the exemplary embodiment of a delivery system shown in FIG. 1. The illustrated delivery system 100 can be configured as a multi-catheter guiding system for delivering an interventional device 102 to a targeted treatment area (e.g., through transapical, transfemoral, or transthoracic introduction). By way of example, the interventional device 102 can be a replacement valve (e.g., mitral, tricuspid, aortic, or pulmonary valve), tissue fixation device (e.g., valve clip), chordae tendineae (i.e., chord) replacement or repair device, annuloplasty ring, occluding device, septal defect repair device, spacer, suture device, or other interventional device suitable for use in a structural heart procedure. For purpose of illustration and not limitation, reference is made herein to a delivery system for a tissue fixation device.

The delivery system 100 has proximal end 120 and a distal end 122. The system 100 includes a guide catheter 300 having a proximal end portion 301, and a distal end portion 302. As described further herein, the proximal end portion 301 includes a proximal end port 303 and the distal end portion 302 includes a distal end port 304, and an inner lumen extends in fluid communication between the proximal end port 303 and the distal end port 304. In accordance with another aspect of the disclosed subject matter, and as described further below, the guide catheter 300 can be a steerable guide catheter.

The system 100 further includes a delivery catheter 104 extending through the inner lumen 128 of the guide catheter 300. For purpose of example, and as embodied herein, the delivery catheter 104 can include a steerable sleeve 106 with an inner shaft 108 disposed therein, as described further herein. The steerable sleeve 106 can be positioned radially within the guide catheter 300, and inner shaft 108 can be positioned radially within the sleeve 106, as shown. An annular space 124 is defined between an outer surface 127 of the delivery catheter 104 and an inner surface 319 of the guide catheter 300. As embodied herein, outer surface 127 of the deliver catheter 108 can be an outer surface of the steerable sleeve 106. The inner shaft 108 can be translatable within the steerable sleeve 106, and the steerable sleeve 106 can be translatable within the guide catheter 300.

While the system 100 is depicted with a guide catheter 300 and a delivery catheter 104 having a steerable sleeve 106 and inner shaft 108 disposed therein, those of skill in the art will recognize that delivery systems in accordance with the disclosed subject matter can have alternate configurations. For purpose of example and not limitation, delivery systems can include multiple guide catheters, such as an outer guide catheter and one or more inner guide catheters disposed therein. Alternatively, the delivery system can be a single integral component.

For purpose of example, and as described further below, a fixation device 102 can be removably coupled to a distal end of the delivery catheter and configured for fixation to leaflets of a native valve. Manipulation of the guide catheter 300 and/or sleeve 106 can enable the fixation device 102 to be directed through a patient's vasculature to a targeted treatment area of the patient's heart. As embodied herein, angling of the guide catheter 300 and the inner sleeve 106 can be achieved using the guide catheter handle 309 and the sleeve handle 112 attached to the proximal ends of the guide catheter 300 and the sleeve 106, respectively. As shown, the guide catheter handle 309 is coupled to the proximal end of the guide catheter 300, and the sleeve handle 112 is coupled to the proximal end of the sleeve 106. The sleeve 106 is inserted through the guide catheter handle 309 to position the sleeve 106 radially within the guide catheter 300. The inner shaft 108 is inserted through the sleeve handle 112 to position the inner shaft 108 radially within the sleeve 106 and the guide catheter 300. As embodied herein, an inner shaft can be assembled within a sleeve to limit translation within the sleeve. For example, an inner shaft can have a larger profile than the sleeve at sections of the inner shaft proximal and/or distal to the sleeve according to the order of construction/assembly.

Figure 2:
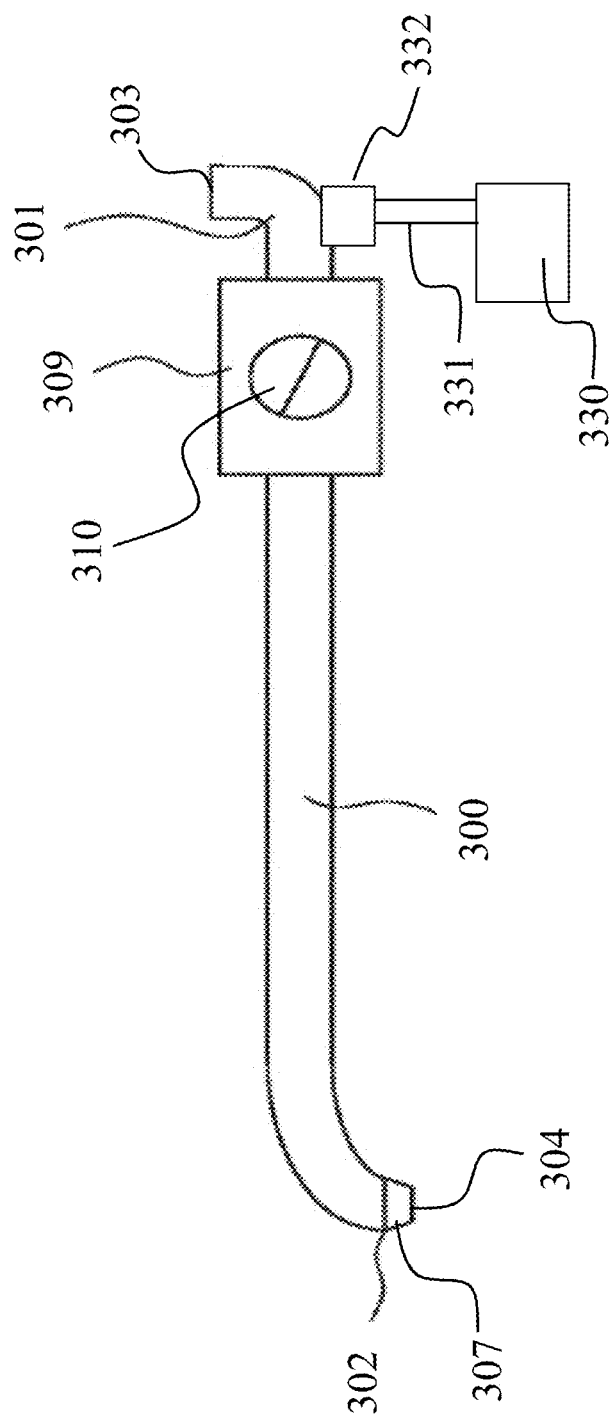
FIG. 2 is a schematic view of an exemplary guide catheter suitable for use in a delivery system in accordance with the disclosed subject matter.
Figure 3:
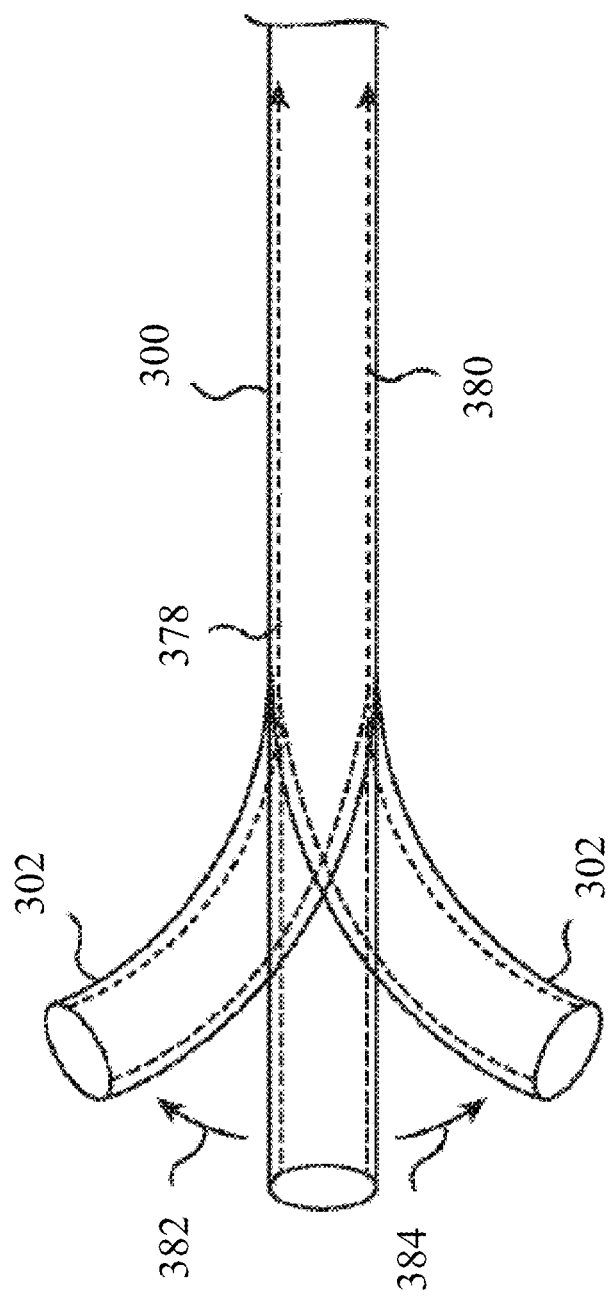
FIG. 3 is a partial detail view depicting various positions of the distal end portion of the guide catheter of FIG. 2.

For purpose of illustration, and not limitation, reference is made to the exemplary embodiment of a guide catheter 300 shown in FIGS. 2 and 3. The guide catheter 300 includes a proximal end portion 301 having a proximal end port 303 and a distal end portion 302 having a distal end port 304. An inner surface 319 of the guide catheter 300 defines an inner lumen extending in fluid communication between the proximal end port 303 and the distal end port 304. The distal end portion 302 of the guide catheter 300 includes a plurality flow passages 205 as described further herein.

As embodied herein, guide catheter 300 can have a generally tubular shape, and can be comprised of a material which provides hoop strength while maintaining flexibility and kink resistance, such as a braided laminated material. Such material can include stainless steel braided or coiled wire embedded in a polymer such as polyurethane, polyester, polyether block amide (e.g., Pebax) or the like, Grilamid TR55, and AESNO to name a few. At least a length of the guide catheter 300 can include a braided reinforcement. For purpose of example and not limitation, a distal end portion of the guide catheter can include a braided reinforcement. To provide further support and hoop strength, a support coil can be disposed within the lumen of the guide catheter 300.

With reference to FIG. 3, guide catheter 300 and/or the sleeve 106 can be a steerable guide catheter and can include steering mechanisms to position the distal end 302 of the guide catheter 300 and/or sleeve 106 in desired directions. The guide catheter 300 can include a steering mechanism having a plurality of cables 378, 380 extending a length of the guide catheter. As shown, the guide catheter 300 can include a first cable 378 slidably disposed in a lumen within the wall of the guide catheter 300 and extending a length of the guide catheter to the distal end portion 302. By applying tension to the cable 378 in the proximal direction, the distal end 302 curves in the direction of the cable 378 as illustrated by arrow 382. Likewise, placement of a second cable 380 along the opposite side of the guide catheter 300 will allow the distal end 302 to be curved in the opposite direction, as illustrated by arrow 384, when tension is applied to the second cable 380.

Thus, the opposed cables 378 and 380 within the walls of the guide catheter 300 can enable the distal end 302 to be steered or bent in opposite directions. As embodied herein, the steering mechanism can include one or more steering knobs 310 and 118 for controlling the tensioning of one or more of the cables 378, 380 running the length of the guide catheter 300 and/or the sleeve 106. This can provide a means of correcting or adjusting a curvature of the guide catheter 300 and/or sleeve 106 within one or more reference planes. For example, if tension is applied to one cable to create a curvature, the curvature can be lessened by applying tension to the diametrically opposite cable. The illustrated embodiment includes two opposing cables. Other embodiments can include a single cable, or can include more than two cables. In addition, cables and associated lumens can be placed in any arrangement, singly or in pairs, symmetrically or non-symmetrically, to enable desired curvature capabilities. Cables can be fixed at any location along the length of the guide catheter 300 by any suitable method, such as gluing, tying, soldering, and the like. When tension is applied to the cable, the curvature forms from the point of attachment of the cable toward the proximal direction. Typically, however, cables are attached near the distal end 302 of the guide catheter 300. Additionally, or alternatively, one or more of the guide catheter 300 or the sleeve 106 can be precurved to provide a desired angling for properly traversing a patient's vasculature in the context of a particular procedural approach.

For example, precurvature or steering of the guide catheter 300 can direct the distal end of the guide catheter 300 to form a first curve, while precurvature or steering of the sleeve 106 can direct the distal end of the sleeve 106 to form a second curve. In this manner, the first curve can differ from that of the second curve so that together the curves form a compound curve. For example, for a mitral valve procedure using a transfemoral approach, the primary curve can have a radius of curvature in the range of 0.8 to 1.0 inches and the secondary curve often has a radius of curvature in the range of 0.050 to 0.750 inches. Advancement of the inner shaft 108 through the sleeve 106 thereby guides the inner shaft 108 through the resulting compound curve, and enables the fixation device 102 to be delivered to the targeted treatment area in a desired orientation. The interventional device 102 can then be actuated, deployed, and/or released through manipulation of the delivery handle 114. As embodied herein, a guide catheter can be configured with precurvature and/or steering functionality so as to accommodate transjugular delivery or other vascular delivery. Alternatively, curvature of both the guide catheter 300 and the sleeve 106 can be oriented in the same direction to provide an even higher angular curvature about a single axis.

The dimensions of the guide catheter 300 can be selected based on the desired use and performance characteristics of the guide catheter 300. For example, smaller outer diameters of the guide catheter 300 can be desirable to facilitate navigation through a patient's vasculature. Additionally, the inner diameter of the guide catheter 300 can be selected, for example, to accommodate the delivery catheter 104 and fixation device 102 within the inner lumen of the guide catheter. The inner diameter of the guide catheter can be varied along the length of the guide catheter. For example, and as described further herein, the distal end portion of the guide catheter can be tapered, and the distal end port can have a smaller inner diameter than an inner diameter of a proximal portion of the guide catheter. For purpose of example, and not limitation, the inner diameter of the distal end port 304 of the guide catheter 300 can be between about 0.205 inches and 0.208 inches. As embodied herein, the inner diameter of the distal end port 304 can be about 0.206 inches. The inner diameter of the distal end port 304 can be selected such that the distal end port 304 has an inner diameter substantially equal to an outer diameter of the delivery catheter 104 along a distal end portion of the delivery catheter 104. As embodied herein, the distal end port 304 can have an inner diameter substantially equal to an outer diameter of the steerable sleeve 106 of the delivery catheter 104 along a distal end portion of the delivery catheter 104.

In accordance with the disclosed subject matter, the system 100 further includes a pressure sensor 330 proximate the proximal end portion 301 of the guide catheter 300. The pressure sensor 330 is in fluid communication with the annular space 124 to monitor fluid pressure within the annular space, as described further herein. The pressure sensor can be placed in fluid communication with the annular space 124 using any suitable means. For purpose of example, and as embodied herein, the proximal end portion 301 of the guide catheter 300 can include a luer connector 332 in fluid communication with the annular space. The pressure sensor 330 can be removably connectable to the luer connector 332, for example, using tubing 331. For purpose of example, the length of tubing 331 can be selected such that the pressure sensor can be positioned at the same height as the patient's heart. Additionally or alternatively, the pressure sensor 330 can be removably connected to the luer connector 332 without tubing 331. A pressure offset can be applied if the pressure sensor 330 is positioned at a different vertical height from the patient's heart to account for changes in pressure due to gravitational forces. The tubing 331 used can have a lumen cross sectional area greater than the minimum flow area of the annular space 124.

Those of skill in the art will recognize that various pressure sensors are known in the art. Any suitable pressure sensor can be used with the delivery systems described herein. For purpose of example, and as embodied herein, the pressure sensor can be a pressure transducer. As described further herein, a pressure sensor capable of detecting changes in pressure as small as about 5 mmHg can be selected. As described further herein, the pressure sensor 330 proximate the proximal end portion of the guide catheter 300 can detect changes in pressure transmitted through the annular space 124 from exterior of the distal end 302 of the guide catheter.

For purpose of example, and as embodied herein, the proximal end portion 301 of the guide catheter 300 can include a hemostasis valve 148 to seal a proximal end of the annular space. The hemostasis valve 148 can be configured to reduce the risk of air introduction and to prevent back bleeding during use of the system. As embodied herein, the hemostasis valve 148 can form a seal between the proximal end 301 of the guide catheter 300 and an outer surface of the delivery catheter 104.

Figure 4A:
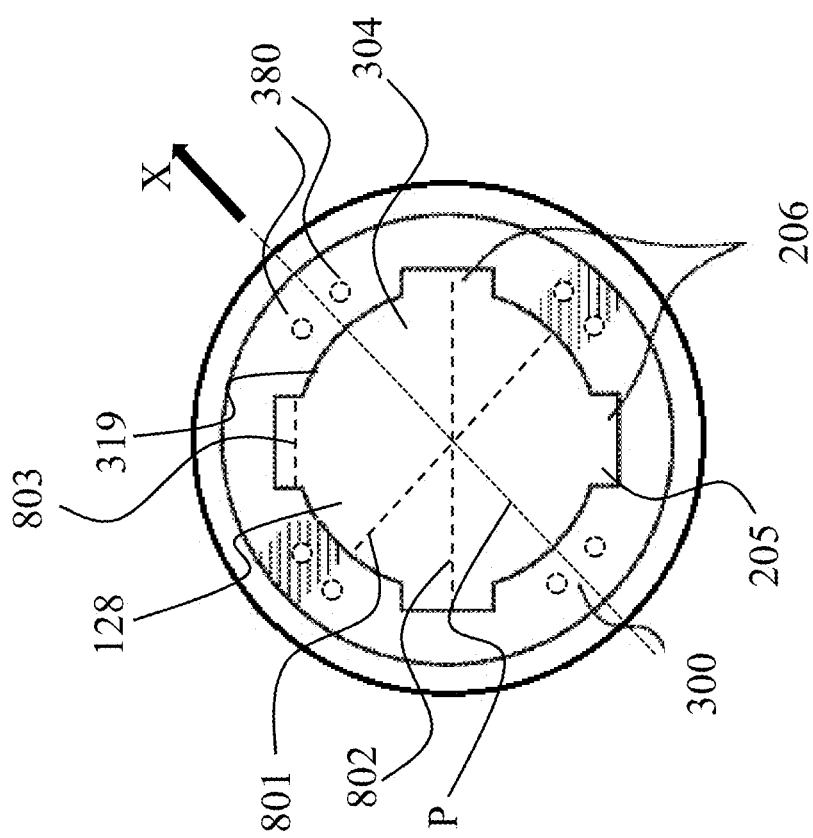
FIG. 4A is an end view of the guide catheter of FIG. 2, depicting the arrangement of flow passages and cables.
Figure 4B:
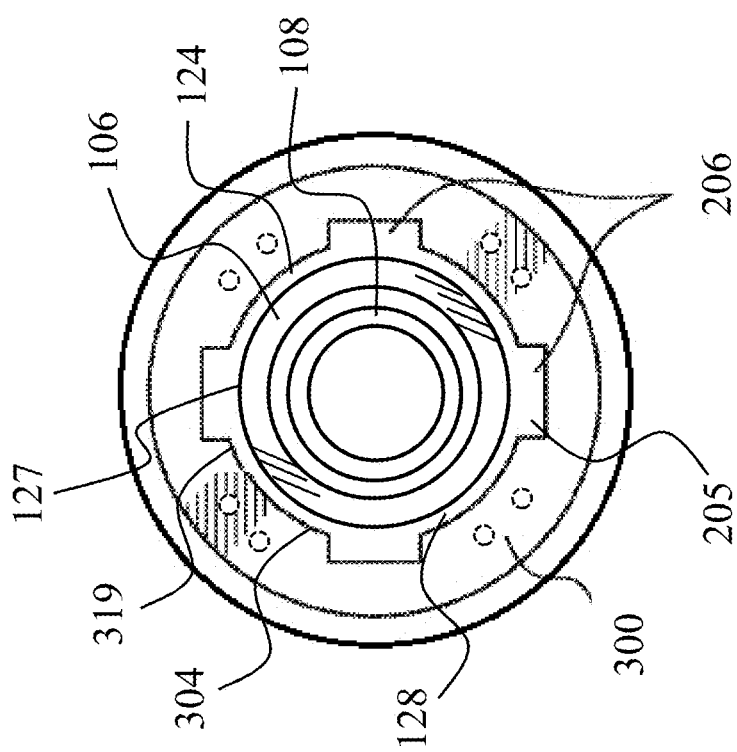
FIG. 4B is a partial cross-sectional view of the delivery system of FIG. 1, taken along line 4B-4B, as depicted in FIG. 1.

With reference to FIGS. 4A and 4B, the guide catheter 300 includes a plurality of flow passages 205 in fluid communication between an exterior of the distal end portion 302 of the guide catheter 300 and an annular space 124 defined between an outer surface 127 of the delivery catheter 104 and an inner surface 319 of the guide catheter 300. In accordance with an aspect of the disclosed subject matter, the plurality of flow passages 205 can collectively have a total flow area between the exterior of the distal end portion 302 and the annular space 124 of between about 0.0021 in$^2$ and 0.0031 in$^2$. For purpose of example, and as embodied herein, the flow passages can include four flow channels 206 spaced about a perimeter of the distal end port 304. Additionally, or alternatively, the plurality of flow passages 205 can include a number of flow openings defined through a wall of the guide catheter, as described further herein.

The configuration of the flow passages 205 can be selected to provide the desired total flow area in communication with the annular space 124 of sufficient size to accurately monitor pressure exterior of the distal end portion, such as an atrial pressure, using a pressure sensor proximate the proximal end portion of the guide catheter, as described further herein. For example, and for purpose of measuring atrial pressure, it has been determined that a fluid column equivalent to that of a 5 Fr catheter is sufficient to obtain accurate atrial pressure measurements. See Gaemperli, O., et al., (2011). Acute hemodynamic changes after percutaneous mitral valve repair: Relation to mid-term outcomes. Heart, 98(2), 126-132, doi:10.1136/heartjn1-2011-300705, the content of which is hereby incorporated by reference in its entirety.

The flow passages 205 can have any suitable shape in end view, including an arcuate shape, substantially triangular shape, or square shape. For purpose of example, and as embodied herein, the flow passages can include four flow channels 206, each having a generally rectangular shape in end view. The dimensions of the flow passages 206 can be selected to provide the desired total flow area, as noted above. For example, and with four flow channels 206 forming the flow passages, each channel can have a width 803 of between about 0.056 inches and 0.062 inches, and a depth measured from the perimeter of the distal port 304 of between about 0.009 inches and 0.0125 inches. For purpose of example, and with reference to FIG. 4A, the depth of each flow channel can be calculated by subtracting the guide catheter inner diameter 801 from the channel-to-channel dimension 802 and dividing the difference by two. As embodied herein, each flow channel can have a width 803 of about 0.059 inches and a depth of about 0.011 inches.

As will be understood by those of skill in the art, the number of flow passages 206, shape of flow passages 206, and dimensions of the flow passages 206 can be selected to achieve the desired total flow area. For example, as the number of flow passages 206 increases, the dimensions of each respective flow passage 206 can decrease such that the total flow area between the exterior of the distal end portion and the annular space is between about 0.0021 in$^2$ and 0.0031 in$^2$.

With reference to FIG. 4A, the steering mechanism described above having a plurality of cables 380 extending a length of the guide catheter 300 can be seen within the sidewall of the guide catheter 300. As described above, applying tension to cables 380 can cause the distal end portion of guide catheter 300 to bend or curve in direction X within reference plane P. For purpose of example and not limitation, each flow channel 206 can be offset circumferentially about the perimeter of the distal end port 304 from the reference plane P. As embodied herein, each flow channel can be offset circumferentially by about 45 degrees from the reference plane P. The circumferential offset of the flow channels 206 can help maintain adequate flow area in the annular space during insertion and manipulation of the delivery system.

The flow passages 205, including flow channels 206, can be formed or incorporated into the wall of the guide catheter 300, such as by extrusion, or can be a separate layer positioned within the guide catheter 300. Furthermore, the flow passages 205 can extend the entire length of the guide catheter 300 or can extend along one or more portions of the length of the catheter. For purpose of example and as embodied herein, the flow passages 205 can extend along a length of the distal end portion of the guide catheter.

Figure 5:
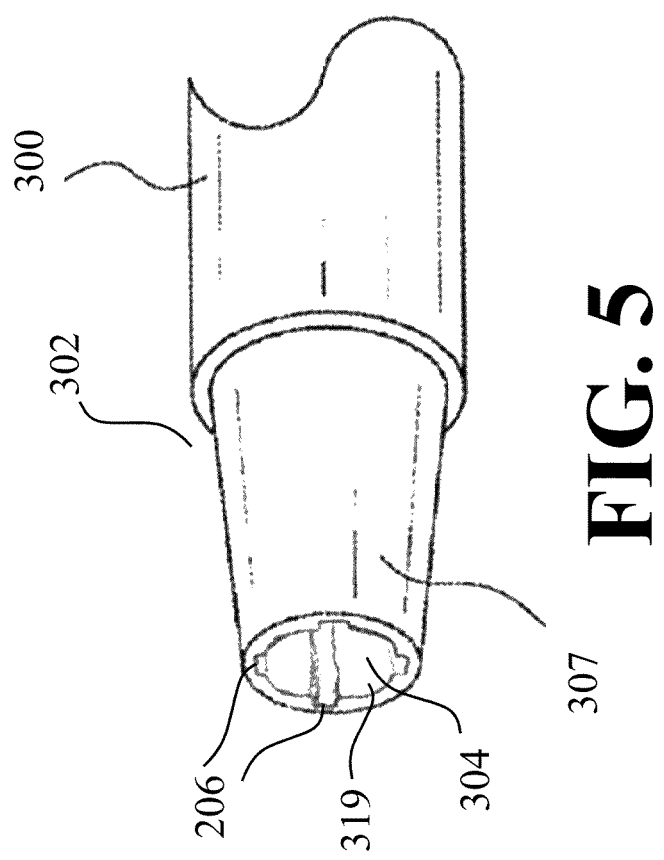
FIG. 5 is a partial detail view of a distal end portion of the guide catheter of FIG. 2.

With reference to FIG. 5, the distal end 302 of the guide catheter 300 can be tapered. As embodied herein, the distal end 302 can include a distal tip member 307 having the distal end port 304 and flow channels 206 defined therein. As embodied herein, the flow channels 206 can run the length of the distal tip member 307. Additionally or alternatively, the flow channels 206 can extend any suitable length from the exterior of the distal end portion 302 proximally along the length of the distal end portion and/or along at least a portion of the intermediate length of the guide catheter 300. The length and location of the flow channels 206 along the length of the guide catheter can be selected to maintain sufficient flow area in communication with the annular space along the length of the guide catheter 300.

The material properties of the distal tip member 307 can be selected based on the desired performance characteristics of the distal tip. For purpose of example and not limitation, the distal tip member 307 can have a durometer hardness measurement of between about 40 D and about 55 D or greater. The distal tip can be made of any suitable material, including polyurethane, polyester, polyether block amide (e.g., Pebax) or the like, Grilamid TR55, and AESNO, or various composite materials used in the construction of catheters. For purpose of example, and as embodied herein, the distal tip can be made of polyether block amide having a durometer hardness measurement of 55 D.

The material properties, including hardness, of the distal tip member 307 and/or distal end 302 can be selected to maintain the desired stiffness and other performance characteristics of the distal tip member 307 and/or distal end 302. For example, including flow channels in the distal tip member 307 can reduce the stiffness of the distal tip member 307 as compared to other distal tip members of similar dimensions and construction but without flow channels, as material is removed from the distal tip to define the flow channels therein. A stiffer material having a higher durometer hardness measurement can be used to compensate for the change in stiffness that can be caused by the use of flow channels in the distal tip.

Figure 6:
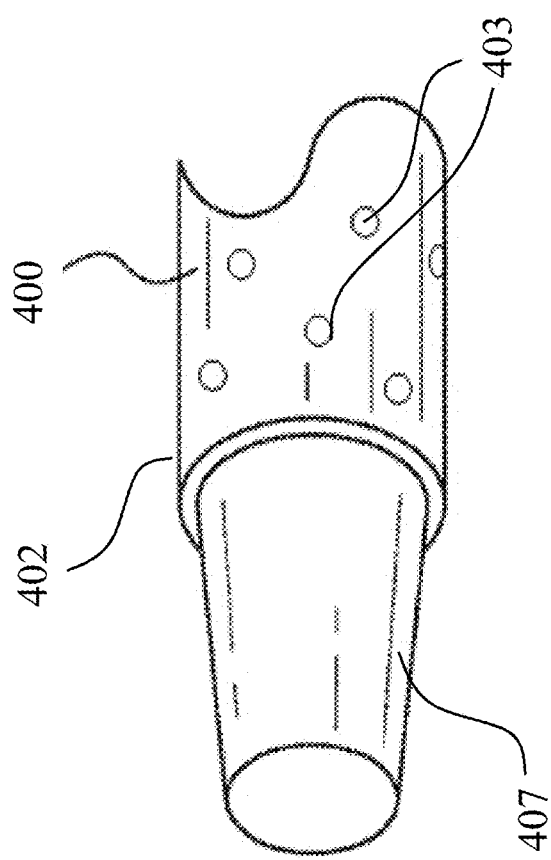
FIG. 6 is a partial detail view of a distal end portion of a guide catheter in accordance with another aspect of the disclosed subject matter.

In accordance with another aspect of the disclosed subject matter, and with reference to FIG. 6, the plurality of flow passages 205 can include a number of flow openings 403 defined through a wall of the guide catheter in fluid communication between the exterior of the distal end portion and the annular space. Flow openings 403 can be used in addition to, or as an alternative to, the flow channels described above. For purpose of example, and as embodied herein, the flow openings 403 can be generally circular in plan view. The flow openings 403 can be defined along a desired length of the guide catheter 300. For example, and as embodied herein, the flow openings can be defined along a length of the guide catheter proximal to the distal tip member 407. As described above, the shape, size, and number of flow openings 403 can be selected such that the total flow area between the exterior of the distal end portion and the annular space is between about 0.0021 in$^2$ and 0.0031 in$^2$.

Additional examples and details related to delivery devices for directing an interventional device to a targeted treatment area, including steering systems, fixation devices, valves, handles, and deployment mechanisms, are described in U.S. Pat. Nos. 7,666,204, 7,563,267, U.S. Patent Application Publication No. 2015/0103804 and U.S. Patent Application Publication No. 2017/0100250, the disclosures of each of which are incorporated herein in their entirety by this reference.

As described above, systems in accordance with the disclosed subject matter can be used in a variety of cardiac procedures, such as a mitral valve replacement, tricuspid valve repair or replacement, chordae tendineae repair or replacement, septal defect repair, occlusion, leaflet modification, leaflet plication, or other cardiac procedure where the monitoring of blood pressure or other hemodynamic properties is desired. FIG. 6 illustrates a transfemoral approach using a delivery system 600 in a procedure requiring access to the left side of the heart, such as a mitral valve repair or replacement procedure. As shown, an interventional device 602 is delivered through the femoral vein by passing an inner shaft 608, to which the interventional device 602 is coupled, through a guide catheter 604 and a sleeve 606. The interventional device 602 is passed through the inferior vena cava 60, into the right atrium 62, through the inter-atrial septum 64 via a puncture, and into the left atrium 66. When necessary or desired, the interventional device 602 can then be directed across the mitral annulus 68 and into the left ventricle 70 via translation of the inner shaft 608. As shown, the steering functionality of the guide catheter 604 and/or sleeve 606, combined with the translatability of the sleeve 606 through the guide catheter 604 and the translatability of the inner shaft 608 through the sleeve 606, enables positioning of the interventional device 602 at the targeted treatment area.

Figure 7:
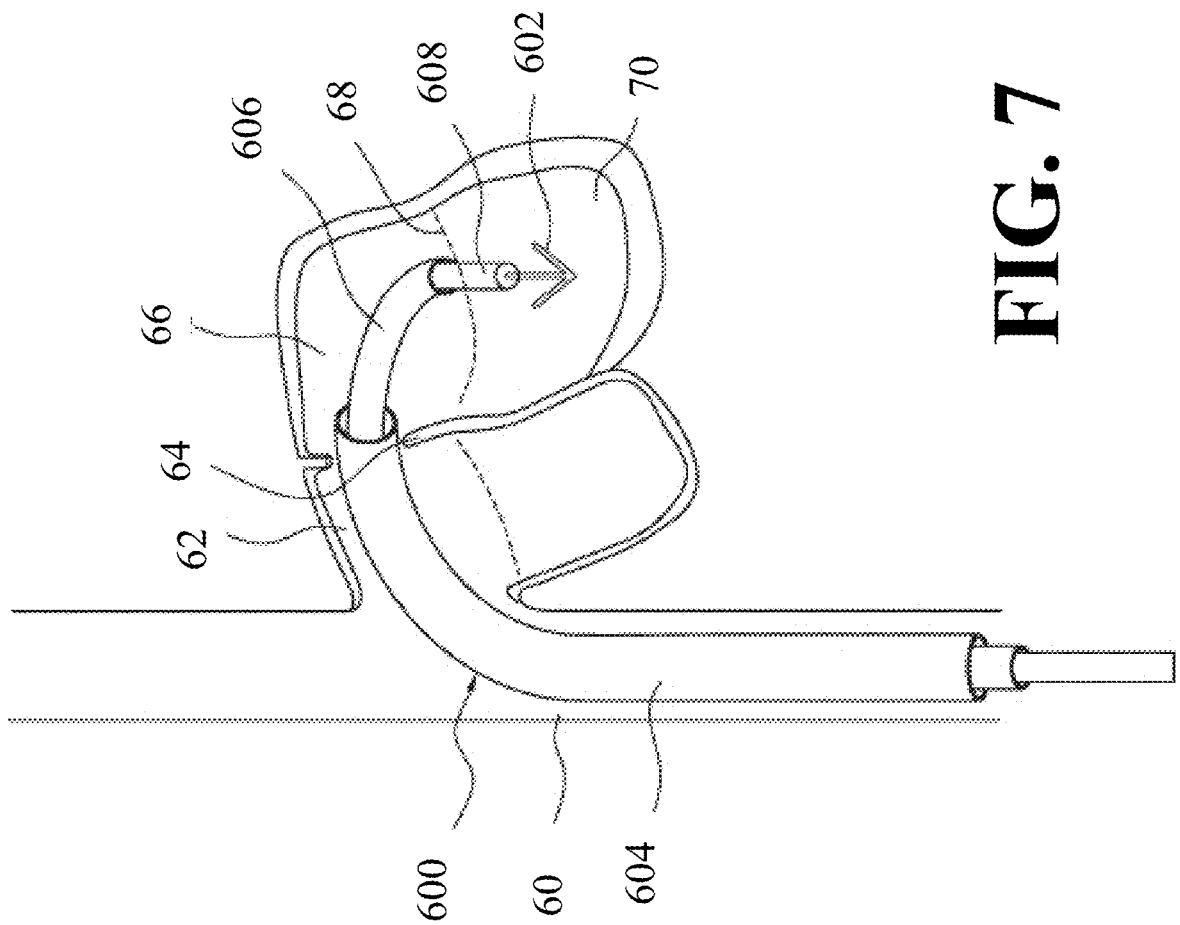
FIG. 7 illustrates a schematic view of a transfemoral approach for delivering an interventional device and/or performing an interventional procedure.
Figure 8:
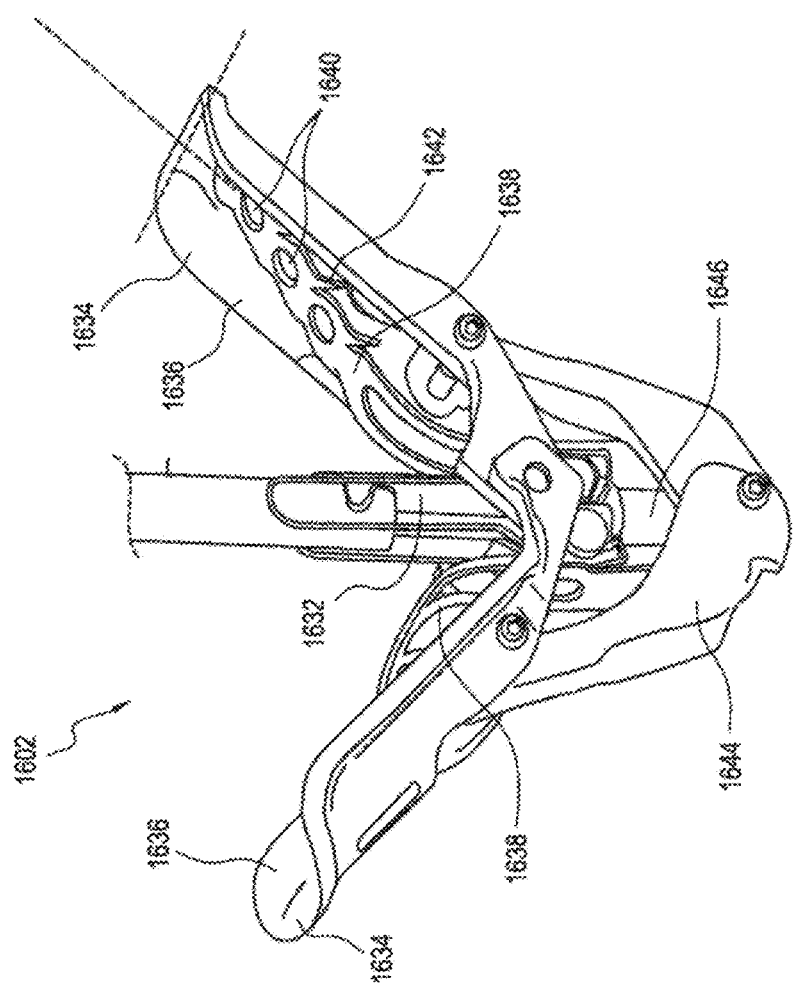
FIG. 8 illustrates an exemplary fixation device suitable for use in a delivery system in accordance with the disclosed subject matter.

FIG. 7 illustrates an embodiment of a fixation device that can be adapted for use in systems in accordance with the disclosed subject matter. The fixation device, or clip, 1602 includes a coupling member 1632 and a pair of opposed distal elements 1634, the distal elements 1634 being formed as elongate arms rotatably connected to the coupling member 1632. The engagement surfaces 1636 of the distal elements 1634 have a cupped or concave shape to surface area in contact with tissue and to assist in grasping and holding valve leaflets when deployed.

In an embodiment suitable for mitral valve repair, the transverse width across engagement surfaces 1636 (which determines the width of tissue engaged) is at least about 2 mm, usually 3-10 mm, and preferably about 4-6 mm. The distal elements 1634 are configured to engage a length of tissue of about 4-10 mm, and preferably about 6-8 mm along the longitudinal axis of the distal elements 1634. The distal elements 1634 can include a plurality of openings to enhance grip and to promote tissue ingrowth following implantation.

When deployed, valve leaflets are grasped between the distal elements 1634 and a set of proximal elements 1638, which are resiliently cantilevered from coupling member 1632. The proximal elements 1638 are resiliently biased toward the distal elements 1634. Each of the proximal elements 1638 is shaped and positioned to be at least partially recessed within the concavity of the corresponding distal element 1634 when no tissue is present. The proximal elements 1638 include a plurality of openings 1640 and scalloped side edges 1642 to increase grip on tissue.

The clip 1602 also includes an actuation mechanism 1644 formed from two linking legs each rotatably joined with one of the distal elements 1634 and rotatably joined at an opposite end to a stud 1646. As the stud 1646 is moved axially, the legs of the actuation mechanism 1644 are rotated, which also rotates the distal elements 1634 between closed, open and inverted positions. Likewise, immobilization of the stud 1646 holds the legs of the actuation mechanism 1644 in place to lock the distal elements 1634 in a desired position.

In the open position, the clip 1602 can engage the tissue to be approximated. During deployment in a mitral valve repair procedure, the distal elements 1634 are oriented to be perpendicular to the line of coaptation, and are then positioned so that the engagement surfaces 1636 contact the ventricular surface of the valve leaflets. The proximal elements 1638 remain on the atrial side of the valve leaflets so that the leaflets can be grasped between the proximal elements 1638 and distal elements 1634. Once the clip 1602 has been properly positioned, the proximal elements 1638 are lowered toward the engagement surfaces 1636 (e.g., by releasing tension on attached control lines) so that the leaflets are held therebetween.

After the leaflets have been captured between the proximal elements 1638 and distal elements 1634 in a desired arrangement, the distal elements 1634 can be rotatably moved toward a closed position, and the clip 1602 can be decoupled from a shaft and/or any other delivery mechanisms. Embodiments of tissue fixation clips are further described in U.S. Pat. Nos. 7,666,204 and 7,563,267, the disclosures of each of which are incorporated herein by this reference in their entirety.

Systems of the disclosed subject matter have demonstrated desired performance characteristics, including adequate configuration and flow area of the annular space such that pressure waves originating exterior of the distal end portion of the guide catheter can be transmitted through the annular space along the length of the guide catheter and can be monitored by the pressure sensor proximate the proximal end of the guide catheter. For purpose of understanding and not limitation, data is provided to demonstrate various operational characteristics achieved by the systems disclosed herein. For purpose of understanding, laboratory measurements were collected to demonstrate the performance of systems in accordance with the disclosed subject matter under laboratory conditions, as described below.

FIG. 9 depicts dimensions of the delivery systems tested. The Lo test group included 5 systems with the dimensions shown. The inner diameter 801 of the distal end port, or "Soft Tip ID," was measured as 0.205 inches for the five Lo samples tested. The "Channel to Channel" dimension 802 was measured as 0.226 inches for the five Lo samples tested, which corresponds with a flow channel depth of 0.0105 inches. The flow channel width 803 was measured as 0.057 inches for the five Lo samples tested.

Likewise, the inner diameter 801 of the distal end port, or "Soft Tip ID," was measured as 0.206 inches for the five Nominal samples tested. The "Channel to Channel" dimension 802 was measured as 0.229 inches for the five Nominal samples tested, which corresponds with a flow channel depth of 0.0115 inches. The flow channel width 803 was measured as 0.060 inches for the five Nominal samples tested.

The flow channels 806 were offset circumferentially by about 45 degrees from the guide catheter bend reference plane for each of the samples tested in both the Nominal and Lo groups.

A 5 Fr reference catheter was tested with each test unit as a control. Reference catheters were inspected before use. If kinked or damaged, a new catheter was used. 5 Fr diagnostic catheters are an acceptable control per current industry standards for invasive left atrial hemodynamic monitoring.

Five sample units per group were tested under three test conditions, simulating 60 BPM, 30 BPM, and 100 BPM, respectively. Thus, each test group included a total of 15 data points used for statistical analysis. Tolerance interval analysis was used, and the one-sided upper tolerance limit was calculated and compared to an acceptance limit. The use of a tolerance interval (also referred to as a confidence and reliability interval) is a conservative choice for a coverage interval compared to a confidence interval. This is because it makes an inference on the proportion of individual values within the population at a specified confidence level, as opposed to making an inference on just the location of the average value.

Data outputs from the testing include pressure profiles from the 5 Fr reference catheter and the tested guide catheter across five cardiac cycles for each test configuration/condition. Descriptive statistics (i.e. mean±standard deviation of the waveform maximum, mean, and minimum) from the average of the five cardiac cycles was calculated for both the reference catheter and tested guide catheter. Max, Mean, and Min values can be clinically relevant values for assessment. The minimum value can be used to ensure the overall amplitude of the waveform is not dampened.

Figure 10:
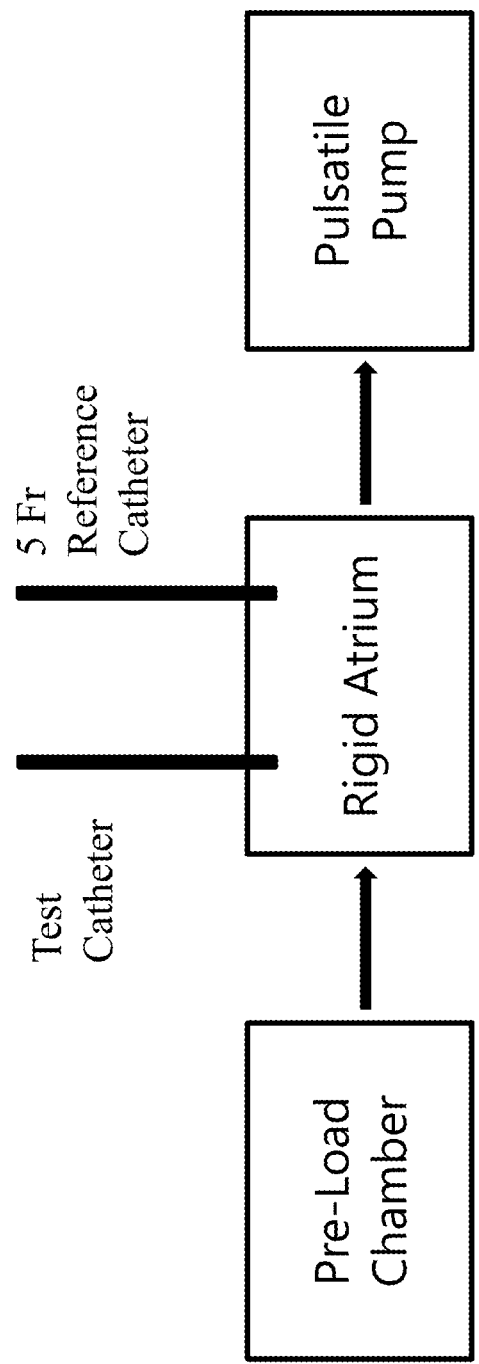
FIG. 10 is a block diagram of a laboratory testing model used to measure certain performance characteristics of delivery systems in accordance with the disclosed subject matter.

Test Model: With reference to FIG. 10, the atrial pressure testing model is comprised of three main components: a preload chamber, rigid atrial chamber, and pulsatile pump. The pre-load chamber serves as a fluid reservoir to passively fill the simulated atrium (LA) of heart and most importantly simulates pre-load pressures into LA from pulmonary flow. The rigid atrial chamber is 3-D printed to include several access points for secure entry of SGC device, reference catheter and endoscope. the atrium is connected to a pulsatile pump, which controls the stroke volume, flow rate, and output phase ratio.

To ensure the test model produced waveforms appropriate for assessment of LAP monitoring devices, pressure waveforms from the model were compared to human LAP waveforms. Waveforms were downloaded Fast Fourier transform (FFT) analysis was conducted to break down the pressure signals, as a function of time, into the frequency domain such that the two signals could be compared in a similar format. The analysis resulted in the model producing waveforms of equal frequency to clinical data; therefore, the afore described model is appropriate for use.

Results: Under all test conditions, the LAP (max, mean, and min values) measured by the Nominal and Lo samples are <5 mmHg of the LAP measured by the reference catheter.

With reference to FIG. 11A, the results of the Shapiro-Wilk W test show the P-values for SGC07-Nominal max, mean, and min groups are 0.051, 0.452, and 0.246, respectively. Since the P values are ≥0.010, there is insufficient evidence to reject the assumption that the data were drawn from a normal distribution. Therefore, it is acceptable compare the one-sided upper tolerance limit at 95/95 confidence and reliability to the acceptance limit of 5 mmHg. All calculated upper tolerance limits are less than 5 mmHg.

With reference to FIG. 11B, the results of the Shapiro-Wilk W test show the P-values for SGC07-Low max, mean, and min groups are 0.026, 0.161, and 0.025, respectively. Since the P values are ≥0.010, there is insufficient evidence to reject the assumption that the data were drawn from a normal distribution. Therefore, it is acceptable compare the one-sided upper tolerance limit at 95/95 confidence and reliability to the acceptance limit of 5 mmHg. All calculated upper tolerance limits are less than 5 mmHg.

Accordingly, systems according to the disclosed subject matter demonstrated adequate configuration and size to enable pressure monitoring capability as compared to a 5 Fr reference catheter under the laboratory test conditions described above.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A delivery system for a fixation device, comprising:
a guide catheter comprising a proximal end portion having a proximal end port, a distal end portion having a distal end port, and an inner surface defining an inner lumen extending in fluid communication between the proximal end port and the distal end port;
a delivery catheter extending through the inner lumen of the guide catheter to define an annular space between an outer surface of the delivery catheter and the inner surface of the guide catheter; and
a pressure sensor proximate the proximal end portion of the guide catheter in fluid communication with the annular space to monitor fluid pressure within the annular space,
wherein the distal end portion of the guide catheter includes a distal tip member having a distal end port defined by an inner perimeter surface, the distal tip member comprising a plurality of flow passages in fluid communication between an exterior of the distal end portion of the guide catheter and the annular space, the plurality of flow passages comprising a number of flow channels recessed in and spaced about the inner perimeter surface of the distal end port.

2. The delivery system of claim 1, wherein the plurality of flow passages collectively have a total flow area between the exterior of the distal end portion and the annular space of between about 0.0021 in$^2$ and 0.0031 in$^2$.

3. The delivery system of claim 1, further comprising a fixation device removably coupled to a distal end of the delivery catheter and configured for fixation to leaflets of a native valve.

4. The delivery system of claim 1, wherein the number of flow channels are spaced equally about the inner perimeter surface of the distal end port.

5. The delivery system of claim 1, wherein the number of flow channels comprise four flow channels.

6. The delivery system of claim 1, wherein each flow channel has a width of between about 0.056 and about 0.062 inches.

7. The delivery system of claim 1, wherein each flow channel has a depth from the inner perimeter surface of the distal end port of between about 0.009 and about 0.0125 inches.

8. The delivery system of claim 1, wherein the distal end port has an inner diameter substantially equal to an outer diameter along a distal end portion of the delivery catheter.

9. The delivery system of claim 8, wherein the inner diameter is between about 0.204 inches and about 0.209 inches.

10. The delivery system of claim 1, wherein the distal tip member has durometer hardness measurement of 55 D.

11. The delivery system of claim 1, wherein the distal tip member is made of polyether block amide.

12. The delivery system of claim 1, wherein the guide catheter is a steerable guide catheter comprising a steering mechanism including a plurality of cables extending a length of the guide catheter, the steering mechanism adapted to bend the distal end portion of the guide catheter in at least one reference plane.

13. The delivery system of claim 12, wherein each flow channel is offset circumferentially about the inner perimeter surface of the distal end port from the reference plane.

14. The delivery system of claim 13, wherein each flow channel is offset circumferentially by about 45° from the reference plane.

15. The delivery system of claim 1, wherein the proximal end portion of the guide catheter further comprises a luer connector in fluid communication with the annular space.

16. The delivery system of claim 15, wherein the pressure sensor is removably connectable to the luer connector.

17. The delivery system of claim 1, wherein the pressure sensor is a pressure transducer.

18. The delivery system of claim 1, wherein the proximal end portion further comprises a hemostasis valve to seal a proximal end of the annual space.

19. The delivery system of claim 1, wherein the plurality of flow passages comprise a number of flow openings defined through a wall of the guide catheter in fluid communication between the exterior of the distal end portion and the annular space.

20. The delivery system of claim 1, wherein the distal end portion of the guide catheter comprises a braided reinforcement.

* * * * *